(12) United States Patent
McCall

(10) Patent No.: US 7,670,289 B1
(45) Date of Patent: *Mar. 2, 2010

(54) DRESSING AND INTEGRATED SYSTEM FOR DETECTION OF FLUID LOSS

(76) Inventor: Kenneth Shawn McCall, 313 N. Cedar, Owasso, OK (US) 74055

( * ) Notice: Subject to any disclaimer, the term of this patent is extended or adjusted under 35 U.S.C. 154(b) by 134 days.

This patent is subject to a terminal disclaimer.

(21) Appl. No.: 11/832,274

(22) Filed: Aug. 1, 2007

Related U.S. Application Data

(63) Continuation-in-part of application No. 11/306,947, filed on Jan. 17, 2006.

(51) Int. Cl.
*A61B 5/0265* (2006.01)
*A61B 5/00* (2006.01)
*A61M 5/00* (2006.01)

(52) U.S. Cl. .................. 600/371; 210/739; 210/645; 210/646; 210/649; 210/650; 210/651; 600/362

(58) Field of Classification Search .................. 210/600, 210/634, 645–646, 649–651, 739–741, 744–745, 210/767, 194, 195.1, 195.2, 252, 257.1, 572.2; 422/44–48; 604/1–11; 600/371, 362

See application file for complete search history.

(56) References Cited

U.S. PATENT DOCUMENTS

| | | |
|---|---|---|
| 3,399,971 A | 9/1968 | Kita |
| 4,122,838 A | 10/1978 | Leonard |
| 4,239,495 A | 12/1980 | Gindler et al. |
| 4,350,155 A | 9/1982 | Thompson |
| 4,378,808 A | 4/1983 | Lichtenstein |
| 4,602,249 A | 7/1986 | Abbott |
| 4,619,653 A | 10/1986 | Fischell |
| 4,699,615 A | 10/1987 | Fischell et al. |
| 4,717,378 A | 1/1988 | Perrault et al. |

(Continued)

FOREIGN PATENT DOCUMENTS

WO    WO 99/24145    * 5/1999

(Continued)

OTHER PUBLICATIONS

Melloni, June L.. Melloni's Pocket Medical Dictionary: Illustrated. (2003). The Parthenon Publishing Group. p. 340.*

(Continued)

*Primary Examiner*—Krishnan S Menon
*Assistant Examiner*—Marjorie Christian
(74) *Attorney, Agent, or Firm*—Head, Johnson & Kachigian, P.C.

(57) ABSTRACT

A fluid loss detection device for dressings at pre-existing port sites, catheter sites, operative sites, ostomy sites, drain sites, line sites such as those utilized in hemodialysis, wound sites, or other areas for which monitoring of fluid or blood loss is medically indicated. The detection device includes a patch having a primary loop circuit and an early warning alarm circuit loop. In one embodiment, closure of the early warning alarm circuit loop activates an alarm. The alarm may be connected directly to the patch and sound locally or may be activated remotely via radio transmission. The detection device may additionally cause a medical device such as a hemodialysis system to shut down.

10 Claims, 7 Drawing Sheets

U.S. PATENT DOCUMENTS

| | | | |
|---|---|---|---|
| 4,731,051 | A | 3/1988 | Fischell |
| 4,784,645 | A | 11/1988 | Fischell |
| 4,787,398 | A | 11/1988 | Garcia et al. |
| 5,153,827 | A | 10/1992 | Coutre et al. |
| 5,399,445 | A | 3/1995 | Tinker |
| 5,468,621 | A | 11/1995 | Kojima et al. |
| 5,557,263 | A | 9/1996 | Fisher et al. |
| 5,790,036 | A | 8/1998 | Fisher et al. |
| 6,057,689 | A | 5/2000 | Saadat |
| 6,689,100 | B2 | 2/2004 | Connelly et al. |
| 6,752,785 | B2 | 6/2004 | Van Antwerp et al. |
| 6,764,465 | B2 | 7/2004 | Chen |
| 6,846,303 | B2 | 1/2005 | Eakins et al. |
| 6,878,132 | B2 | 4/2005 | Kipfer |
| 6,921,383 | B2 | 7/2005 | Vitello |
| 6,942,643 | B2 | 9/2005 | Eakins et al. |
| 2005/0010265 | A1* | 1/2005 | Baru et al. .................... 607/48 |
| 2005/0038325 | A1* | 2/2005 | Moll .......................... 600/300 |
| 2007/0293748 | A1* | 12/2007 | Engvall et al. .............. 600/371 |

FOREIGN PATENT DOCUMENTS

| | | | |
|---|---|---|---|
| WO | WO99/24145 | * | 5/1999 |
| WO | WO2006/001759 | * | 1/2006 |

OTHER PUBLICATIONS

Redsense Medical (description of the sensor device) [online] Retrieved Feb. 6, 2009 from the Internet <URL:http://www.redsensemedical.com/Pages/Default.aspx?PageID=2>.*

Redsense Medical User Manual—English (Jun. 28, 2008), Retrieved Feb. 6, 2009 from the Internet <URL:http://www.redsensemedical.com/Pages/ListPressItems.aspx>.*

"Catastrophic Hemorrhage from Venous Needle Dislodgement During Hemodialysis: Continued Risk of Avoidable Death and Progress Toward a Solution"; Stephen Sandroni; American Society of Nephrology Renal Week 2008 (publications), p. 891A-892A; PUB354.

"New Estimates of Fatal Incidents"; Redsense Medical AB, http://www.redsensemedical.com/Pages/ShowNews.aspx?NewsID=62.

"Potential Benefits and Risks of Hemodialysis"; Your Total Health; http://yourtotalhealth.ivillage.com/hemodialysis.html?pageNum=5.

"Keep An Eye on Your Needle", Jane Hurst, RN, KidneyTimes, http://www.kidneytimes.com/article.php?id=20081217152602.

"What Kind of Infections Can Occur in Hemodialysis Patients?", AAKP, http://www.aakp.org/aakp-library/infections-in-hemodialysis-patients/.

Dr. Robert A. Mactier and Dr. David P. Worth, "Minimizing the Risk of Venous Needle Dislodgement During Hemodialysis".

Discussion of Venous Needle Dislodgement During Hemodialysis: An Unresolved Risk of Catastrophic Hemorrhage:, Dr. Stephen Sandroni (Hemodialysis International, Jan. 2005; 9:102), European Dialysis & Transplant Nurses Association European Renal Care Association; http:/www.edtnaerca.org/pages/education/journalclub/summary2005_2.php.

"Venous Needle Dislodgement: How to Mnimise the Risks", Jean-Pierre Van Waeleghem et al.; Journal of Renal Care 2008, p. 163-168.

"Recommendations for Preventing Transmission of Infections Among Chronic Hemodialysis Patients", MMWR, Apr. 27, 2001/SO(RROS); 1-43; http://www.cdc.gov/MMWR/preview/mmwrhtml/rr5005a1.htm.

"Venous Needle Dislodgement (VND), How to Minimize the Risks", EDTNA/ERCA Recommendations for Renal Nurses.

* cited by examiner

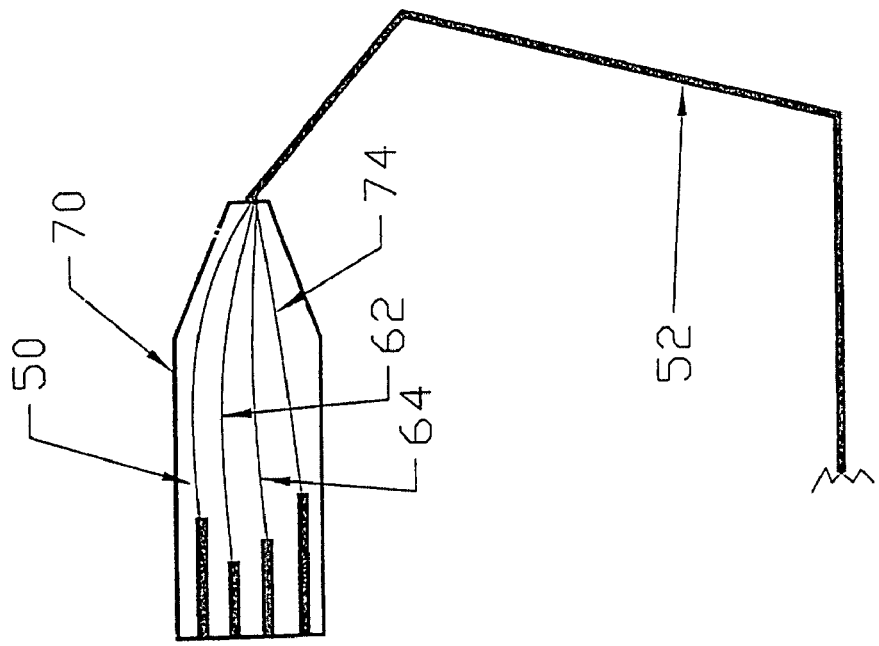
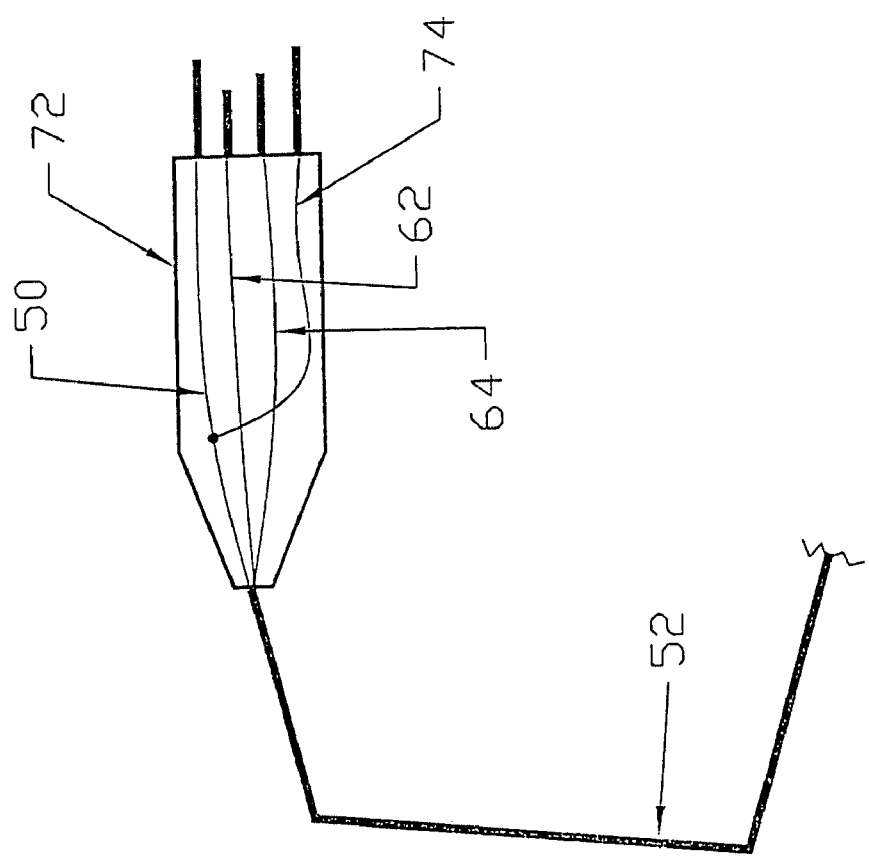
Fig. 4

DRESSING AND INTEGRATED SYSTEM FOR DETECTION OF FLUID LOSS

CROSS-REFERENCE

This application is a continuation-in-part patent application of U.S. patent application Ser. No. 11/306,947 filed Jan. 17, 2006, incorporated in its entirety herein by reference.

STATEMENT REGARDING FEDERALLY SPONSORED RESEARCH OR DEVELOPMENT

Not Applicable.

REFERENCE TO A SEQUENCE LISTING, A TABLE, OR A COMPUTER PROGRAM LISTING COMPACT DISC APPENDIX

Not Applicable.

BACKGROUND OF THE INVENTION

1. Field of the Invention

The present invention relates to a detection device for blood and fluid loss, and a method for dressing wounds, drain sites, catheter sites, port sites, and other areas for which monitoring for blood or fluid loss is medically, diagnostically or clinically indicated.

2. Prior Art

There are any number of situations in which the loss of blood or fluid from one or more body locations is medically significant. Hemodialysis, for example, is a known medical procedure through which a person's blood is cleansed of toxins. Hemodialysis is often prescribed when the kidneys no longer function properly for any of a number of reasons. Hemodialysis is typically performed at a hospital or dialysis center although there is interest in, and a trend toward, at-home use. In a dialysis treatment, the patient is connected to a hemodialysis machine via two tubes. The first tube is a blood intake tube and is responsible for removing blood from the patient and transferring it to the machine. When the blood enters the machine, it is cleaned via semi-permeable filters and then is pumped back to the patient through a blood return tubing. Before hemodialysis can be done, a doctor must make an entrance, often called an "access", into the patient's blood vessels. This is sometimes done by minor surgery in the leg, arm or neck. The best access for many patients is called a "fistula". Minor surgery may be performed to join an artery to a vein under the skin to make a larger vessel.

The dialysis process can take several hours for each procedure and may be done more than once per week depending on the condition. Even if done in the supervision of medical professionals, a patient cannot be monitored every minute. Additionally, a blanket or blankets will often be placed on the patient and the patient may attempt to nap or sleep during the procedure.

There have been reports of the return line becoming accidentally dislodged or pulled from the access site in the patient. If the dialysis machine and its accompanying pump continue to operate, blood will be drawn from the patient but will not properly be returned to the patient. If this condition continues, the patient can suffer loss of blood and even death. While the hemodialysis machines have existing pressure sensing devices, they may not sense the condition if the blood continues to pump. Additionally, if the patient is sleeping or if medical personnel are not constantly observing the entire procedure, blood loss may occur until it is discovered.

Several prior attempts have been made relating to various leak detection systems. For example, Van Antwerp et al. (U.S. Pat. No. 6,752,785) show a wide variety of leak detection devices including devices as shown in FIGS. 10(a), 10(b) and 10(c). Each of these devices must be applied to the body of a user before a needle is inserted since each includes an enclosed circular opening. The Van Antwerp devices cannot be installed once the return line is attached to the patient. If the Van Antwerp device was placed on the patient first, it would involve breaking the sterile field which is created and normally desirable on the skin of the patient before insertion of the needle. If the Van Antwerp device were to be placed prior to inserting the needle into the patient, the sterile field of the access site would be compromised, possibly resulting in an infection of the patient's blood.

Accordingly, it would be desirable to provide for protection of hemodialysis patients from exsanguination.

It would be desirable to provide a blood and fluid loss detection device which might be installed, and a method for installing the device, around a pre-existing return line or needle connected to the patient, as well as a pre-existing operative site, a catheter or port site, a drain site, an ostomy site, or a wound site.

It would also be desirable to provide a blood loss detection device and method which is simple and modular in design which could be easily placed or replaced without interruption of treatment.

It would further be desirable to provide a blood loss detection device and method which has both an alarm and a shut-down system which operates in conjunction with or separately from existing devices such as hemodialysis systems.

It would further be desirable to provide a blood loss detection device and method having a modular connection with a sensor system to confirm the modular connection.

It would also be desirable to provide a blood loss detection device having a radio transmission means for wireless communication of alarm information.

SUMMARY OF THE INVENTION

The present invention provides a blood and fluid loss detection device and process for any number of dressing applications such as operative sites, port sites, catheter sites, line sites, drain sites, ostomy sites and wound sites, and which could specifically be utilized with, and operate along with, a hemodialysis system.

The detection device of the present invention includes a patch having a boundary or external edge extending around and circumnavigating the entire patch. The patch and its boundary edge may take many configurations including, but not limited to, a rectangle or circle. The patch may further comprise gauze or other absorbent material, or the patch may fit about a separate dressing.

In one embodiment, the patch also includes a central opening through the patch which forms a target for receipt of a port, tube, catheter, drain, ostomy or other medical line such as a return access site for return blood line from a hemodialysis machine. In at least one location there shall be an opening or slit from internal to external boundary edge to allow post-access placement. Accordingly, the patch forms an enclosure and surrounds the site with the exception of the slit.

A primary loop circuit extends through a multi-conductor cable to the patch and terminates a pair of opposed ends at the slit in the patch. The multi-conductor cable carries the primary loop circuit to a source of voltage. The voltage power supply is, in turn, wired to an audio alarm. Accordingly, the primary loop circuit delivers and provides an operational signal. An early warning alarm loop circuit passes from the multi-conductor cable into the patch and terminates at two ends at the slit. The early warning alarm loop circuit passes from the patch, through the multi-conductor cable, and back to the audio alarm.

In one embodiment, an emergency shut-down circuit loop extends from the multi-conductor cable into the patch and terminates at two ends at the slit. The emergency shut-down circuit loop extends from the multi-conductor cable to a dialysis machine and, in particular, to the blood pump.

The present invention is also modular in design so that the device may be quickly installed, quickly removed, and replaced as desired. The multi-conductor cable extends from the patch and terminates in a male modular connector which cooperates with a female modular connector which is, in turn, connected to a multi-conductor cable from the hemodialysis machine and the component elements thereof.

The invention is designed to detect blood and fluid loss associated with operative sites, port and catheter sites, line and drain sites, ostomy sites and wounds, as well as the blood return system of hemodialysis.

The invention is a boundary designed to encircle the site of a wound, operative incision, port, catheter, ostomy or drain, or a blood return system of hemodialysis. The boundary could have an adhesive backing to maintain proper placement of the detection device during use, but the device could also be attached by any other means that would allow for secure attachment around the site.

The inner and outer boundaries of the detection device will enclose one or more electrical circuits. These circuits will be composed of one primary input conductor and any number of secondary conductors, such as those returning to a separate device, such as a hemodialysis machine. The hemodialysis machine will monitor the return conductors and as long as the status of the conductors remains unchanged, the treatment will proceed. If at some point the machine should detect a status change across any return conductor, it would initiate a proper response to input information. This status change could be a detectable change in the existing physical properties of the conductors such as input voltage or impedance/resistance on existing circuit.

BRIEF DESCRIPTION OF THE DRAWINGS

FIG. 4 is a simple illustration of the modular connectors of the present invention;

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's shape, construction and the arrangement of its components without departing from the spirit and scope of this disclosure. It is understood that the invention is not limited to the embodiments set forth herein for purposes of exemplification.

The disclosure herein may be applied to a number of situations in which it is medically, diagnostically or clinically advisable to monitor blood and fluid loss. The disclosure herein may be utilized at operative sites, drain sites, port sites, catheter sites, wound sites, ostomy sites, or any other bodily location where blood and fluid loss are to be monitored.

Figure 1:
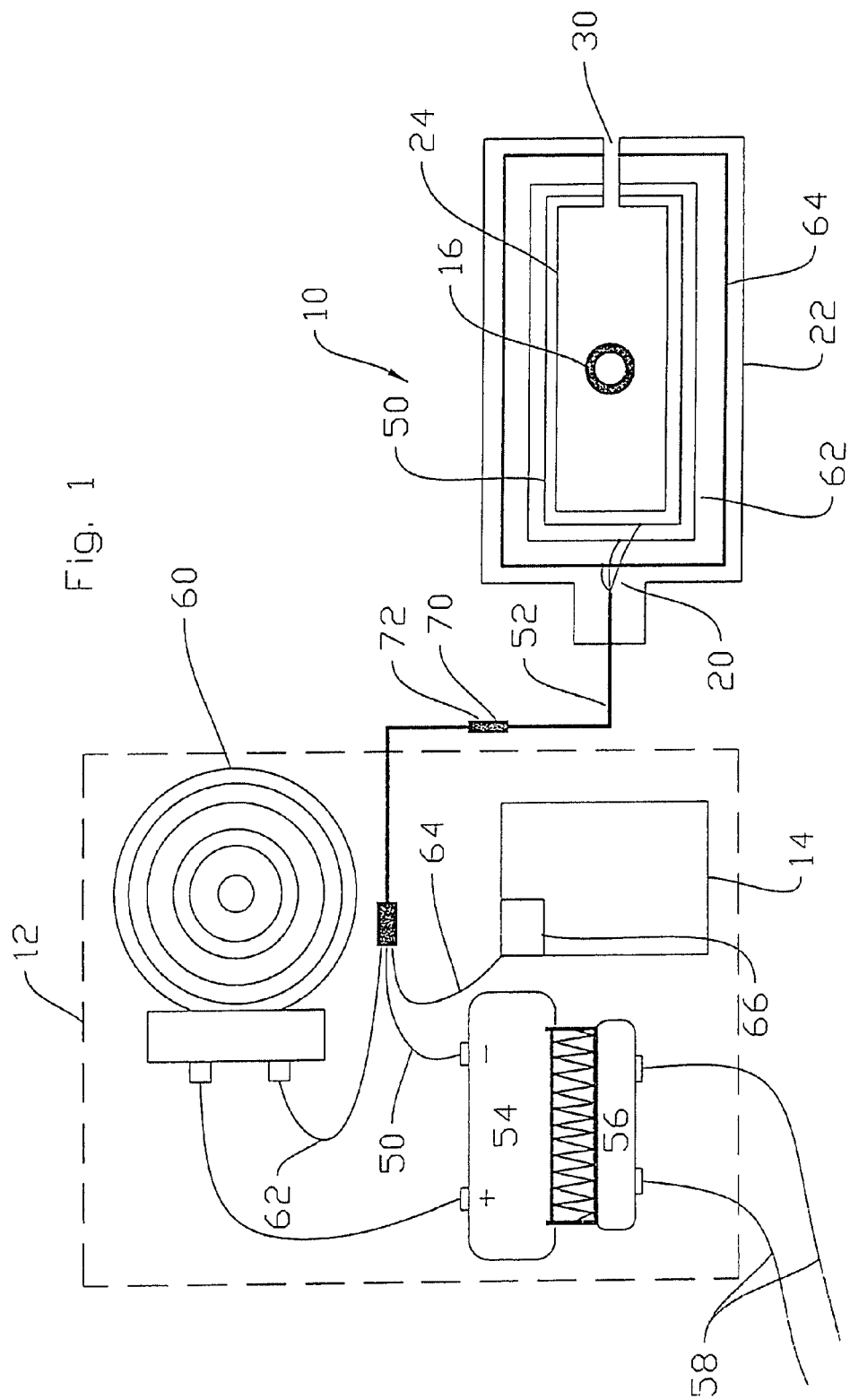
FIG. 1 is a simple diagrammatic view of a blood loss detection device constructed in accordance with the present invention in communication with a hemodialysis system.

Referring to the drawings in detail, FIG. 1 illustrates a simple diagrammatic view of a blood loss detection device 10 constructed in accordance with the present invention.

In one embodiment, the blood loss detection device 10 is utilized with and operates along with a hemodialysis system, represented by dashed lines 12.

Hemodialysis machines and the hemodialysis procedure are both well-known. A patient (not shown) will have a fluid intake tube connected through an access into the blood vessels of the patient. The blood is pumped via a pump (shown diagrammatically by box 14) into and through the hemodialysis machine 12 where the blood is cleansed. The blood is thereafter returned via a blood return line to the patient through a return access site 16.

The detection device 10 of the present invention includes a patch 20 having a boundary or external edge 22 extending around and circumnavigating the entire patch. The patch 20 and its boundary edge 22 may take many configurations including, as shown in FIG. 1, a substantially rectangular form.

The patch 20 also includes an opening 24 through the patch which forms a target for receipt of the return access site 16 and the return blood line (not shown) from the hemodialysis machine 12.

A slit 30 through the patch 20 extends from the boundary edge 22 to the patch opening 24. Accordingly, the patch forms an enclosure and surrounds the return access site 16 with the exception of the slit 30. The ends may be overlapped to form a complete enclosure.

The blood access site monitor consists of a base typically with adhesive backing, would be able to substantially encircle the blood access site, and within its inner and outer boundaries contains the primary input circuit and required number of monitoring circuits. The access site monitoring device or patch should be composed of a permeable material that would facilitate transfer of any blood or fluid across the primary input conductors and monitoring circuits.

Figure 2:
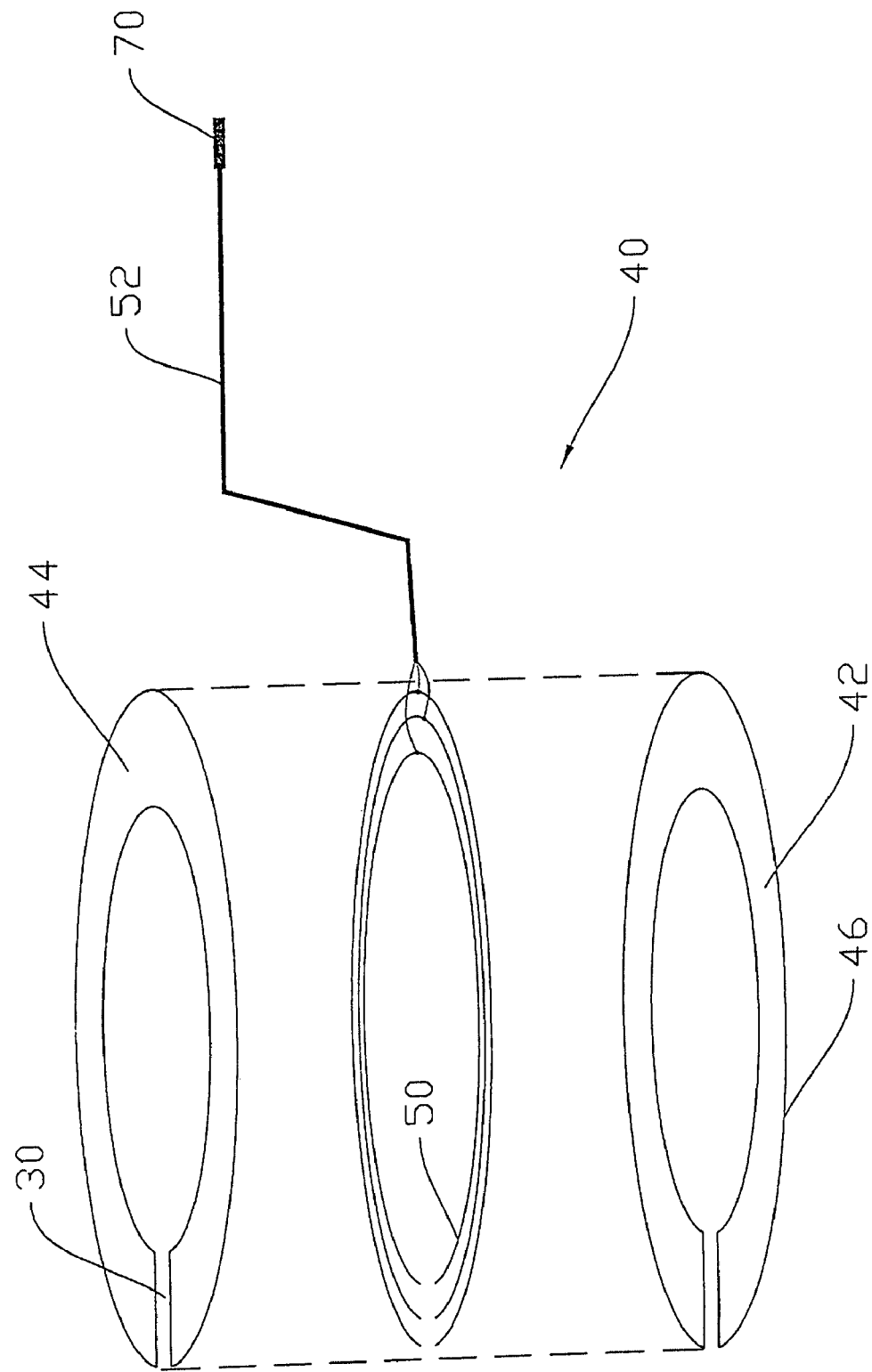
FIG. 2 illustrates an exploded view and FIG. 3 illustrates a top view of an alternate embodiment of the detection device of the present invention.
Figure 3:
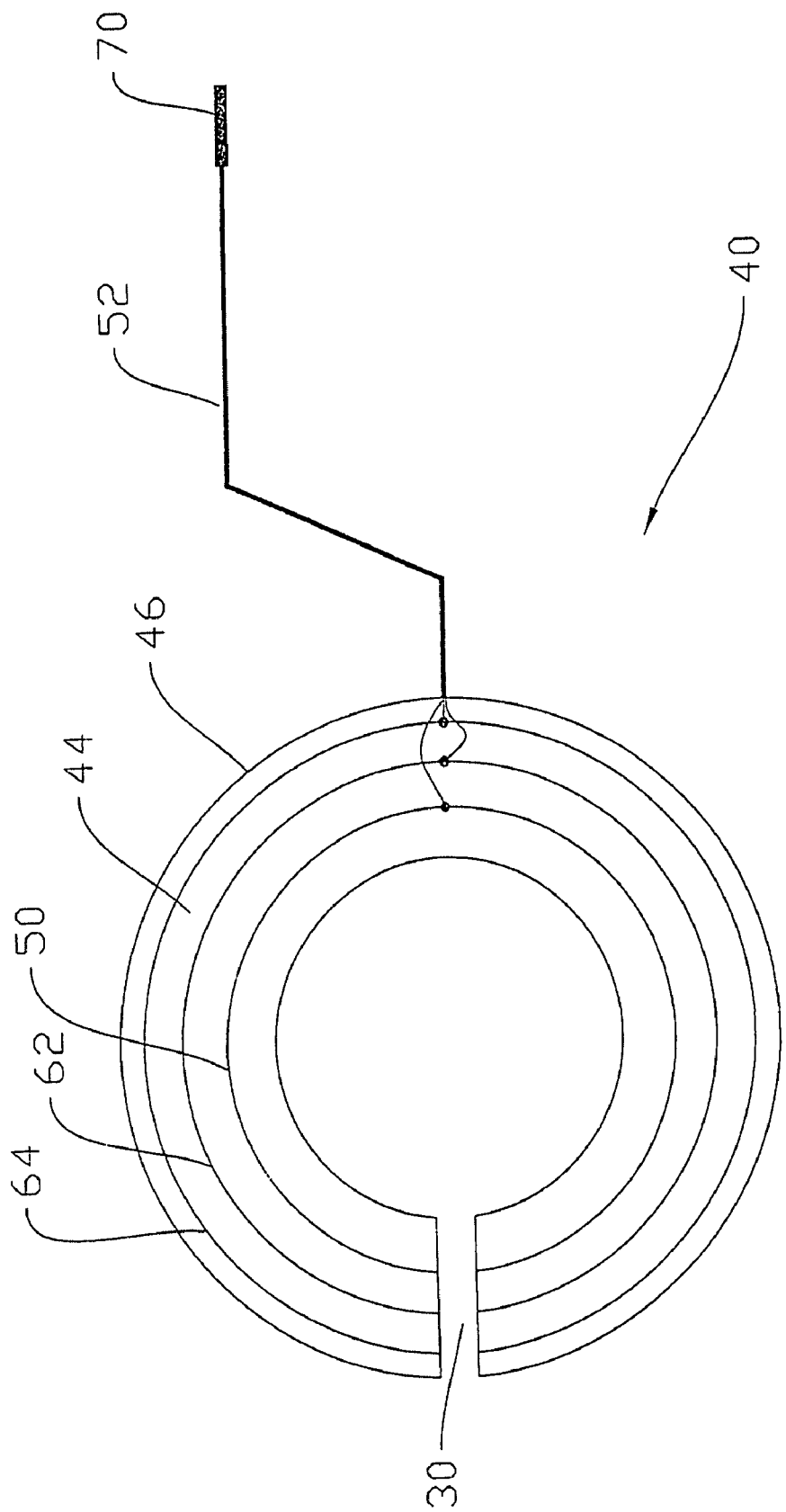

FIGS. 2 and 3 illustrate an alternate embodiment of the detection device 10. FIG. 2 shows an exploded view of an alternate embodiment 40 while FIG. 3 illustrates a top view. The patch 40 includes a first layer 42 having an adhesive base designed to adhere to a skin of a patient. Above the first layer 42 are the electrical conductors to be described. A top layer 44 covers both the electrical conductors and the first layer 42. The boundary edge 46 of the alternate embodiment 40 is in the form of a circle.

Finally, an optional transparent cover (not shown) could be adhesively secured to the top layer 44. The cover might be transparent to allow for visual observation but retain any blood loss.

With reference to FIG. 1 and continuing reference to FIGS. 2 and 3, a primary loop circuit 50 extends through a multi-conductor cable 52 via a primary input loop conductor to the patch (reference numeral 10 in FIG. 1 and reference numeral 40 in FIGS. 2 and 3). The primary input conductor circuit loop 50 terminates at a pair of opposed ends at the slit 30 in the patch. The multi-conductor cable 52 carries the primary loop circuit conductor to a DC voltage power supply 54 which, in turn, is connected to transformer 56 and thereafter connected to alternating current power supply 58. The power supply is, in turn, wired to an audio alarm 60. Accordingly, the primary loop input conductor 50 delivers and provides operational voltage to the detection device 10.

An early warning alarm loop circuit 62 passes from the multi-conductor cable 52 into the patch 20. The early warning alarm loop circuit 62 terminates at two ends at the slit 30. The early warning alarm loop circuit 62 passes from the patch 20 through the multi-conductor cable 52 and back to the audio alarm 60. An emergency shut-down circuit loop 64 extends from the multi-conductor cable 52 to the patch 20. The emergency shut-down circuit loop terminates at two ends at the slit 30.

The emergency shut-down circuit 64 extends through the multi-conductor cable 52 to the dialysis machine 12 and, in particular, to the pump 14. The emergency shut-down circuit includes a switch mechanism 66 to shut down the dialysis machine 12 and, in particular, the pump 14.

The present invention is modular in design so that the blood loss detection device 10 may be quickly installed, removed and replaced as desirable.

The multi-conductor cable 52 extending from the patch 40 terminates in a male modular connector 70. The male modular connector 70 will cooperate with a female modular connector 72 connected to multi-conductor cable 52 which, in turn, is connected to the hemodialysis machine 12 and the component elements previously discussed.

FIG. 4 illustrates the modular connectors with an optional feature of an optional safety electric loop circuit. In addition to the primary loop circuit 50, the early warning alarm circuit 62 and the emergency shut-down circuit 64, the modular connectors include an optional safety loop circuit 74.

Figure 5:
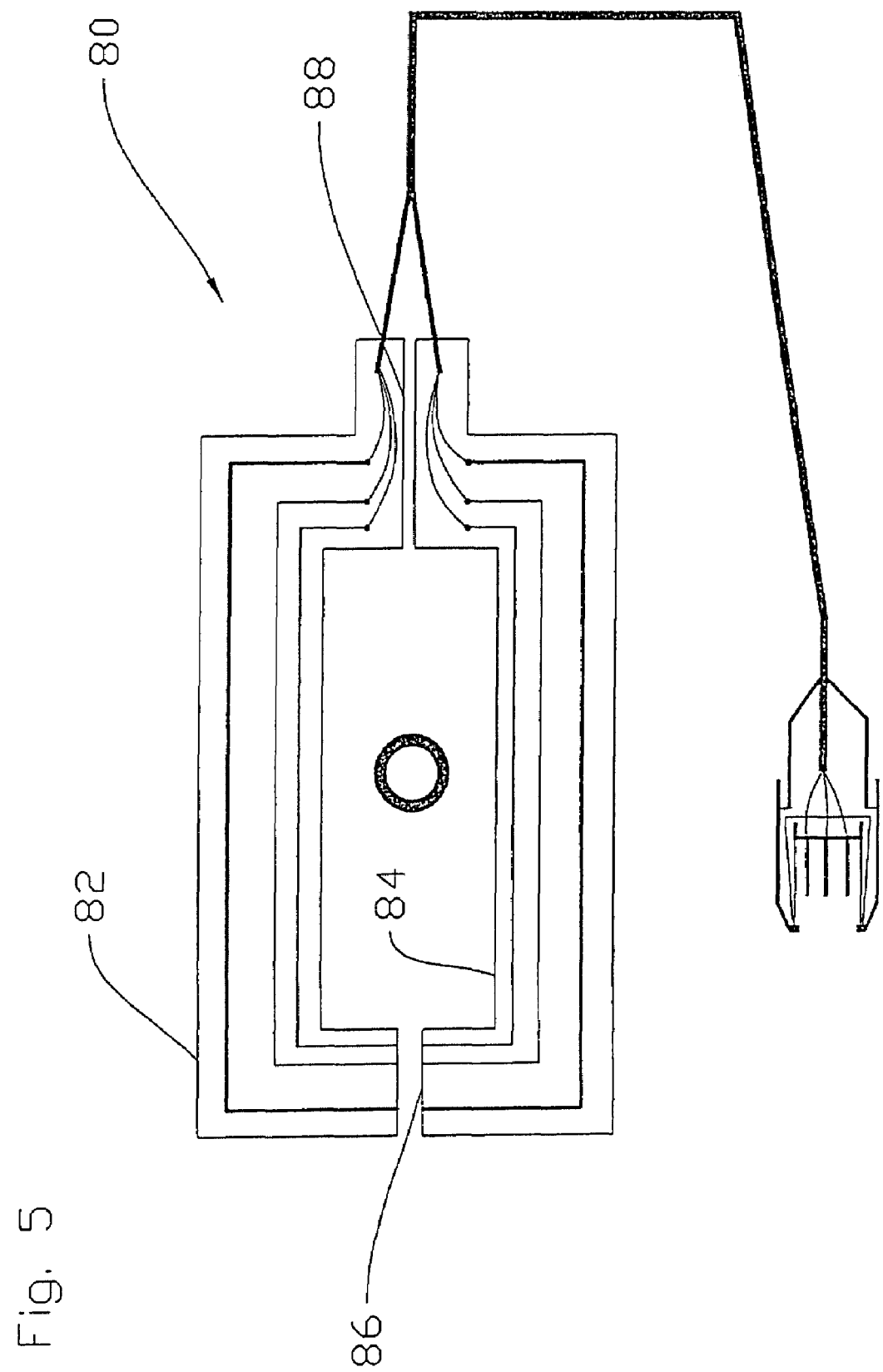
FIG. 5 illustrates a further alternate embodiment of a blood loss detection device (double split design) constructed in accordance with the present invention.
Figure 6:
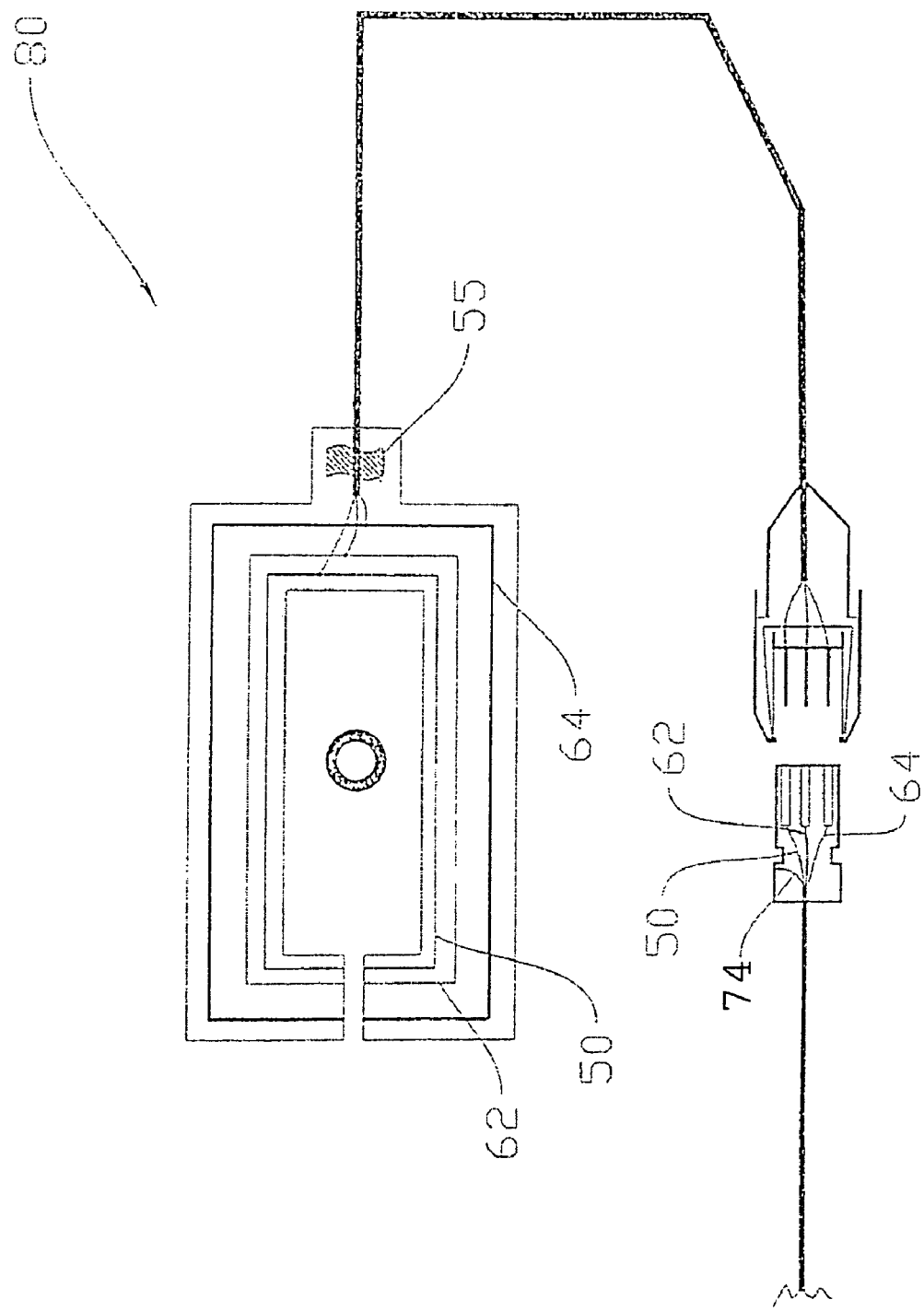
FIG. 6 illustrates a further alternate embodiment of a blood loss detection device with a self-monitoring plug.

FIGS. 5 and 6 show another embodiment of a safety loop modular connector. FIG. 5 shows a further alternate embodiment of the present invention including a patch 80 having a boundary edge 82 and an opening 84. Slits 86 and 88 extend through patch 80 between the boundary edge 82 and the opening 84.

FIG. 5 illustrates a further alternate embodiment 80 of the invention utilizing a double split in the patch and a modular self-monitoring plug.

Figure 7:
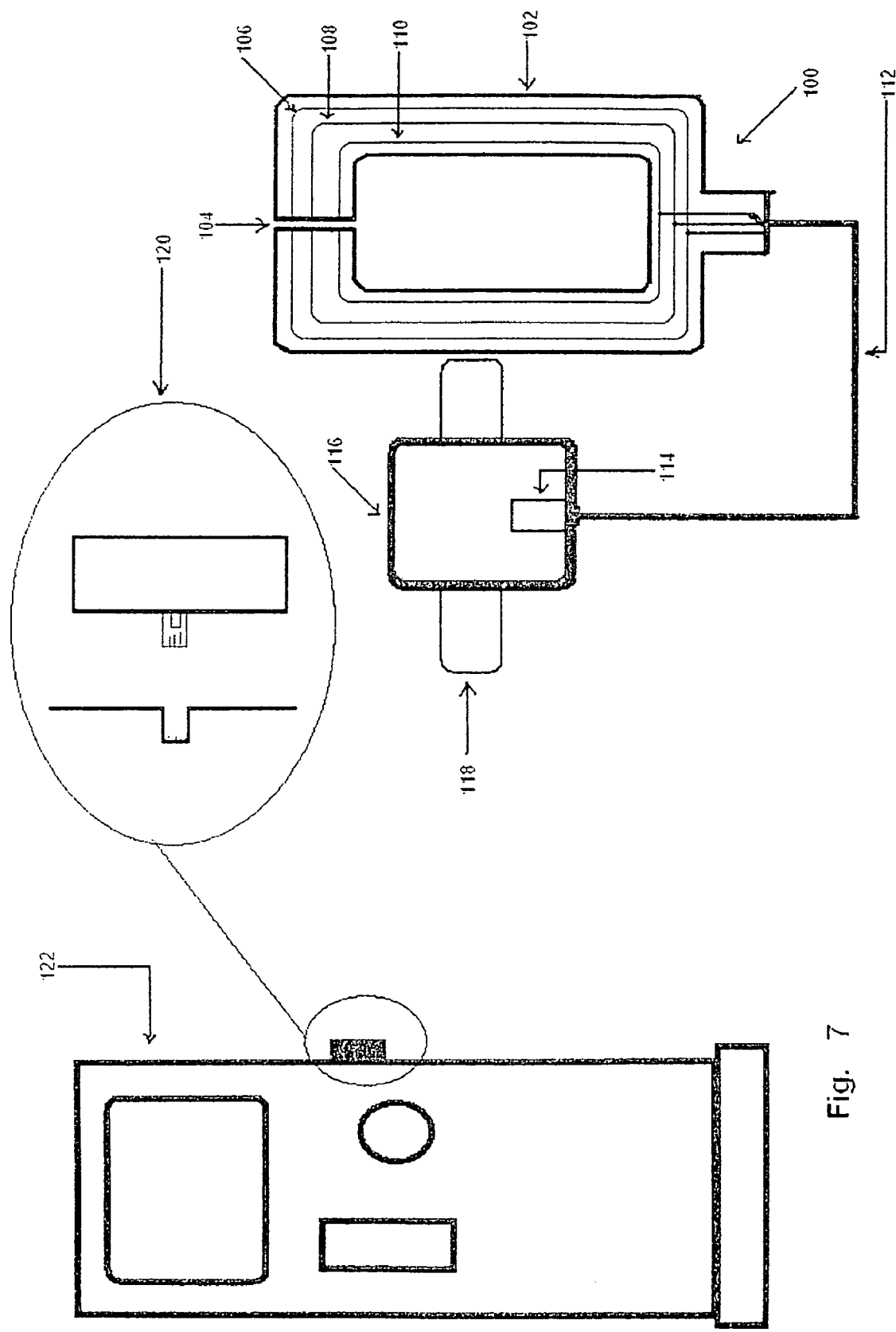
FIG. 7 depicts a simple diagrammatic view of an alternative embodiment of the disclosed device.

FIG. 7 depicts an alternative embodiment of the present invention. Patch 100 has a boundary edge 102 and a slit 104, as well as a primary loop circuit 106, an early warning alarm loop circuit 108, and an emergency shut-down circuit 110. Primary loop circuit 106, early warning alarm loop circuit 108, and emergency shut-down circuit 110 extend through a multi-conductor cable 112 to a male connector plug 114. Male connector plug 114 is in turn connected to radio transmitter 116. Persons skilled in the art will appreciate that radio transmitter 116 may be any suitable device capable of transmitting a radio signal, preferably a low frequency radio signal.

The radio transmitter 116 features adhesive bands 118 for attachment to a patient's limb. It should be appreciated that any self-adhesive or hook-and-loop adhesive may be utilized, and that radio transmitter 116 need not be attached to the patient's body but could alternatively be attached to a chair, bed rail, instrument cart, instrument stand, night stand, or other nearby furnishing or structure.

Still referring to FIG. 7, a radio receiver 120 is situated within range of radio transmitter 116. Persons skilled in the art will appreciate that radio receiver 120 may be any suitable device that is capable of receiving a radio signal, provided that it is compatible with radio transmitter 116. Radio receiver 120 is operably connected to a downstream device 122. Downstream device 122 may be a medical instrument such as a dialysis machine, or an alarm device capable of activation in response to a radio signal received by radio receiver 120.

The patch 100 and accompanying multi-conductor cable 112 and plug 114 could be disposed of after a single use.

For simple description of operation in FIG. 1, the illustrations will be limited to one input conductor and two return or output circuits or conductor. In the illustration, the inner 24 and outer 22 boundaries enclose three conductors—the primary input conductor circuit loop 50, an emergency notification conductor loop 62 and an emergency shut-down conductor loop 64.

As long as the dialysis machine does not sense a change or input voltage on conductor 62 or 64, the treatment would proceed without interruption. If the machine detects a change in the status of conductor 62, it would activate some type of notification alarm and staff could address the problem and treatment would continue uninterrupted. If at any point during treatment, the machine would detect a change in the status of conductor 64, the machine would initiate an alarm and shut down the blood pump, preventing blood flow to the blood return access site.

The device shown in FIG. 6 also includes a tubing clip 55 to retain the needle and fluid tube (not shown) in association with the patch.

A machine connection lead is composed of a multi-conductor cable that originates from control connections within the machine and terminates at a modular female connector. The number of conductors are variable and will depend on the monitoring configuration of the patch/access monitoring device. In the most basic design there would be at least two conductors, the first conductor would provide signal input to the monitoring device/patch and the second would provide a return path to the dialysis machine should a blood loss incident occur. In more advanced designs there would be additional conductors that would communicate other features/embodiments back to the machine for monitoring. In the enclosed details, the machine connection lead would contain four to five conductors. The first conductor 50 would be the signal input conductor or what is referred to as line voltage. The second conductor 62 would be an early warning conductor and would be activated by a small fluid leak. The third conductor 64 would be an emergency shut-down circuit and would only be activated when a larger fluid loss occurs. The fourth conductor 53 and fifth conductor 74 would be utilized in verifying that the modular connectors were properly connected.

As may be appreciated from the foregoing, the present invention may include optional circuits beyond the primary conductor and alarm/shut-down circuits set forth herein.

Whereas, the present invention has been described in relation to the drawings attached hereto, it should be understood that other and further modifications, apart from those shown or suggested herein, may be made within the spirit and scope of this invention.

What is claimed is:

1. A fluid loss detection device, comprising:
   a patch;
   a central opening through said patch so that said patch surrounds said central opening;
   a boundary edge of said patch circumnavigating said patch;

a slit through a portion of said patch, wherein said slit originates at said boundary edge of said patch and terminates approximately at said central opening of said patch;

a primary circuit loop within said patch and defining a first perimeter therein, wherein said primary circuit loop surrounds said central opening, which forms a target for receipt of a return access site;

an early warning alarm circuit loop within said patch and defining a second perimeter therein, wherein said first perimeter is contained within said second perimeter;

an alarm activated by a status change in properties of said early warning alarm circuit loop, wherein said early warning alarm circuit loop is activated by a small blood leak and wherein said emergency shut-down circuit loop is activated by a larger blood loss; and an emergency shut-down circuit loop within said patch and defining a third perimeter therein, wherein said second perimeter is contained within said third perimeter and wherein said primary circuit loop, said early warning alarm circuit loop, and said emergency shut-down circuit loop are in a radial plane formed by said patch.

2. A fluid loss detection device as set forth in claim 1 wherein said patch includes a base for connection to the skin of a patient.

3. A fluid loss detection device as set forth in claim 1 further comprising:

a radio transmitter activated by said status change in properties of said early warning alarm circuit loop; and a radio receiver that is compatible with said radio transmitter and that is operably connected to said alarm.

4. A fluid loss device as set forth in claim 3 wherein said radio transmitter is capable of emitting a low frequency radio signal and wherein said radio receiver is capable of receiving a low frequency radio signal.

5. A method of fluid loss detection, comprising the steps of:

placing a patch having an external boundary edge circumnavigating said patch and a central opening through said patch so that said patch surrounds said central opening;

adhesively securing said patch to a patient;

sensing if fluid causes a change in electrical properties of a primary circuit loop and an early warning alarm circuit loop and thereafter activating an alarm; and sensing if fluid causes a change in electrical properties of an emergency shut-down circuit loop independent from said early warning alarm circuit wherein said primary circuit loop, said early warning alarm circuit loop and said emergency shut-down circuit loop are in a radial plane formed by said patch.

6. A method of fluid loss detection as set forth in claim 5, further comprising the step of, before said patch is placed, wrapping said patch around a pre-existing protrusion in said patient's skin.

7. A method of fluid loss detection as set forth in claim 6, wherein said protrusion is selected from the group consisting of a line, a port, a drain, an ostomy and a catheter.

8. A method of fluid loss detection as set forth in claim 5, further comprising the steps of:

operably attaching said patch to a radio transmitter;

selecting a radio receiver that is compatible with said radio transmitter;

operably attaching said radio receiver to said alarm; and monitoring said radio receiver for activation of said alarm.

9. A method of fluid loss detection as set forth in claim 5, further comprising the steps of:

operably attaching said patch to a radio transmitter;

selecting a radio receiver that is compatible with said radio transmitter;

operably attaching said radio receiver to a medical device;

transmitting a radio signal between said radio transmitter and said radio receiver upon the activation of said alarm; and shutting down said medical device upon the transmission of said radio signal.

10. A method of fluid loss detection as set forth in claim 9, wherein said medical device is a hemodialysis system.

\* \* \* \* \*